(12) United States Patent
Senosiain Peláez et al.

(10) Patent No.: US 9,433,602 B2
(45) Date of Patent: Sep. 6, 2016

(54) COMBINATION AND COMPOSITION FOR TREATING OBESITY

(75) Inventors: Juan Pablo Senosiain Peláez, Mexico City (MX); Gustavo Barranco Hernandez, Mexico City (MX); Raul Garcia Salgado Lopez, Mexico City (MX)

(73) Assignee: LABORATORIOS SENOSIAIN S.A. DE C.V., Mexico City (MX)

( * ) Notice: Subject to any disclaimer, the term of this patent is extended or adjusted under 35 U.S.C. 154(b) by 0 days.

(21) Appl. No.: 13/996,410

(22) PCT Filed: Dec. 16, 2011

(86) PCT No.: PCT/IB2011/055723
§ 371 (c)(1),
(2), (4) Date: Aug. 13, 2013

(87) PCT Pub. No.: WO2012/085785
PCT Pub. Date: Jun. 28, 2012

(65) Prior Publication Data
US 2013/0316005 A1 Nov. 28, 2013

(30) Foreign Application Priority Data

Dec. 21, 2010 (MX) .................. MX/a/2010/014484

(51) Int. Cl.
| | |
|---|---|
| *A61K 31/365* | (2006.01) |
| *C07C 39/21* | (2006.01) |
| *C07D 305/12* | (2006.01) |
| *A61K 31/05* | (2006.01) |
| *A61K 9/16* | (2006.01) |
| *A61K 9/50* | (2006.01) |

(52) U.S. Cl.
CPC .......... *A61K 31/365* (2013.01); *A61K 9/167* (2013.01); *A61K 9/1652* (2013.01); *A61K 9/5047* (2013.01); *A61K 31/05* (2013.01); *C07C 39/21* (2013.01); *C07D 305/12* (2013.01); *A23V 2200/332* (2013.01)

(58) Field of Classification Search
CPC ............ A61K 2300/00; A61K 31/05; A61K 31/365; A61K 9/1652; A61K 9/167; A61K 9/5047; A23V 2200/332
See application file for complete search history.

(56) References Cited

U.S. PATENT DOCUMENTS

| | | | |
|---|---|---|---|
| 2006/0111435 A1 | 5/2006 | Sinclair et al. | |
| 2006/0153889 A1* | 7/2006 | Friel et al. | ............... 424/401 |
| 2007/0264328 A1* | 11/2007 | Ghebre-Sellassie et al. | 424/464 |
| 2010/0196464 A1* | 8/2010 | Kothamasu et al. | ......... 424/451 |

FOREIGN PATENT DOCUMENTS

| | | |
|---|---|---|
| WO | WO 01/00205 A1 | 1/2001 |
| WO | WO 2004/080450 A2 | 9/2004 |
| WO | WO 2007/008548 A2 | 1/2007 |
| WO | WO 2010/045522 A2 | 4/2010 |

OTHER PUBLICATIONS

Rivera et al., Biochemical Pharmacology, 2008, 1-37.*
Yun, "Possible anti-obesity therapeutics from nature—A review," Phytochemistry, vol. 71, 2010, pp. 1625-1641.

* cited by examiner

*Primary Examiner* — Kyle Purdy
(74) *Attorney, Agent, or Firm* — Birch, Stewart, Kolasch & Birch, LLP (57) ABSTRACT

The present invention relates to the pharmaceutical field, especially the field of combination and pharmaceutical compositions that comprise a lipase inhibitor and a phytoalexin and pharmaceutically acceptable vehicles or excipients; the present invention also relates to the method for manufacturing compositions containing the combination and the use of said composition in the treatment of conditions of excess weight, obesity and related health problems.

6 Claims, 8 Drawing Sheets
(8 of 8 Drawing Sheet(s) Filed in Color)

COMBINATION AND COMPOSITION FOR TREATING OBESITY

TECHNICAL FIELD

The present invention has its application in the pharmaceutical field, especially in the field of pharmaceutical combinations and compositions comprising a lipase inhibitor, a phytoalexin and pharmaceutically acceptable excipients or carriers. The present invention also relates to a process for the manufacture of the pharmaceutical composition and the use of such composition for the preparation of a drug product useful in the treatment of overweight, obesity and related health problems.

BACKGROUND OF THE INVENTION

The World Health Organization (WHO) warns that in the world there are more than 1,600 million people with overweight and that number increases exponentially. Also according to the WHO, the number of obese people is more than 700 million.

Previously, it was considered that overweight or obesity were problems that only affected rich countries but the WHO estimates show that overweight and obesity are increasing exponentially in the low and middle income countries. This is due to several factors such as the widespread change of diet towards increased intake of calories, fats, salts and sugars, the trend towards the decrease of physical activity caused by the sedentary nature of the job, changing transportation media and the increase of urbanization.

In Mexico, according to official data, 70% of adults are overweight and even worse, the same percentage is recorded in children between 5 and 11 years old (4.5 million children). The care of people suffering from obesity in Mexico has grown considerably in recent years, in more than 60% since 2000, triplicating the percentage since 1980.

Obesity is a chronic and degenerative disease. In adults, overweight and obesity promote the development of diseases such as hypertension, diabetes mellitus, gout, stroke, heart disease and more. Some scientific research assure that the current childhood obesity will cause, in the coming years, further grow of the population of young adults with diabetes mellitus, hypertension, hyperlipidemia and many other problems related to excess body fat and sedentary lifestyles.

In the case of cardiovascular diseases, it has been observed that the risk of developing coronary disease increases by 20% in overweight people and 50% in obese people.

The risk of developing type 2 diabetes increases by 20% in overweight or obese people.

On the other hand, a body mass index (normal BMI 18.5-24.9) equal or greater than 25 is associated with a higher risk of suffering bone and hip fractures.

Compared with normal weight individuals, those who are overweight and obese have a higher risk of developing asthma and kidney diseases.

Nowadays there are different medications and remedies for the treatment of overweight and obesity, however, to date, there remains a need for drugs that enable weight loss in a short time and without side effects that may put at risk the patient's health.

Initially, the main therapy to be considered is the improvement in the patient's habits, i.e., increasing exercise and having a proper diet. However, when the obesity problem is not solved through this way it requires drug treatment. Most drugs for the treatment of obesity act by decreasing food intake through an appetite suppression mechanism. Such drugs act at the central nervous system (CNS) level and have an anorexigenic effect. For this reason its use is not recommended for long-term treatments.

According to the international consensus, the use of obesity drugs is justified when the diet treatment fails, exercise and behavioral management in patients with BMI>30 Kg/m$^2$ (obese) or BMI>25 Kg/m$^2$ (overweight) and co-morbidity of medical relevance (type 2 diabetes, hypertension, dyslipidemia, arthropathy, and so on).

According to the field of invention, the ideal characteristics of a drug product for the treatment of obesity are:
1. Demonstrated reduction in weight and associated diseases.
2. Tolerable or transient side effects.
3. No major adverse reactions after years of use.
4. Long-term sustained efficacy.
5. Without addictive properties.
6. Known mechanism(s) of action.
7. Affordability.

The drugs used for the treatment of obesity are classified according to their mechanism of action as described below:
Appetite inhibitors or satiety stimulators.
Adrenergic agents: Diethylpropion, Mazindol, Phentermine, Ephedrine.
Selective inhibitors for serotonin uptake: Fluoxetine, Sertraline.
Dual action (adrenergic-serotoninergic): Sibutramine.
Endocannabinoid receptor 1 inhibitors: Rimonabant.
Thermogenics-lipolytics: Ephedrine/Caffeine.
Fat absorption inhibitor or lipase enzyme inhibitor: Orlistat.
Natural products: Resveratrol.

Active agent orlistat belongs to the group of inhibitors of the lipase enzyme. This compound is an off-white waxy solid, easily soluble in chloroform, insoluble in water, with a melting point between 40° C.-48° C.

Orlistat reduces the absorption of fat by the inhibition of pancreatic lipase activity, avoiding the splitting of fats in their simplest components, provoking their disposal without being absorbed. This compound exerts its therapeutic activity in the lumen of the stomach and in the small intestine, forming a covalent bond with the serine in the active site of the gastric and pancreatic lipases.

Orlistat is administered orally at doses not greater than 360 mg per day, given that higher doses do not have a therapeutic effect. Depending on the patient, different doses may be administered which can be from 30 mg, 60 mg, 120 mg to 240 mg. Different medical publications mention that the usual dose is the administration of 120 mg three times per day.

In obese patients with type 2 diabetes, orlistat is used in weight reduction, and thus it helps to achieve a better glycemic control and reduces postprandial increments of triglycerides, cholesterol and free fatty acids. Orlistat provides additional control when being administered in combination with antidiabetic agents such as metformin, sulfonylureas and/or insulin.

In volunteers with normal weight and obese subjects, the systemic exposure to orlistat is minimal. Plasma concentrations of intact orlistat were virtually undetectable (<5 ng/ml) after single administration of 360 mg. In general, plasma concentrations are extremely low (<10 ng/ml or 0.02 µM) with no evidence of accumulation. Studies in people with normal weight or obese have shown that fecal excretion of the unabsorbed drug was the major route of elimination.

Approximately 97% of the administered dose was excreted in feces and 83% of that was unchanged orlistat.

Orlistat adverse reactions are, largely, of gastrointestinal nature and are related to the pharmacological effect of the drug in the 30% decrease of the absorption of ingested fat. The commonly observed events are grease stains, flatulence and secretions, fecal urgency, grease/oily stools, oily evacuation, increased defecation and fecal incontinence. A higher incidence of these effects has been observed with an increase of fat content in the diet.

Similarly it has been determined a decrease in the absorption of vitamin D, E and β-carotene when they are co-administered with orlistat, but serum levels of these vitamins remained within normal limits.

Resveratrol (3,5,4'-trihydroxystilbene) is a phytoalexin present in grapes and derived products such as wine, and other foods like oysters, peanuts and nuts. It is a powerful antioxidant, polyphenolic, with a molecular formula $C_{14}H_{12}O_3$ and molecular weight of 228.25. Is a yellowish white powder, non-hygroscopic, insoluble in water, soluble in alcohol and methanol, insoluble in hydrochloric acid 10% and photosensitive. It naturally exists in the form of cis- and trans-isomer, the most common being the trans-resveratrol found in the skin of grapes.

The mechanism of action of this active agent is not yet defined, although some publications mention that it is capable of stimulating the SIRT1 gene family, which codifies sirtuins (NAD-dependent histone deacetylases), triggering metabolic processes related to the duration of life, which are the same that are triggered with restricted diets, thus mimicking caloric restriction. Thus, it is assumed that a low calorie and low carbohydrate diet can extend life. Resveratrol is capable of inhibiting several inflammatory enzymes including cyclooxygenase and lipoxygenase.

In metabolic regulation, resveratrol allows maintaining the effects of a low calorie diet, without changing the food intake, which may be beneficial in the treatment of obesity.

In animal studies, resveratrol exhibits anti-aging effects, cardioprotective effects (in vitro resveratrol inhibits platelet aggregation), neuroprotective effects (by activating SIRT1 it reduces neurodegenerative diseases), anti-inflammatory and chemopreventive effects and as a metabolic regulator it maintains a low calorie diet, without changing the food intake, which may be beneficial in the treatment of obesity.

In humans, although the trans-resveratrol appears to be well absorbed when taken orally, its bioavailability is relatively low due to its rapid metabolism and renal elimination (half-life of approximately 8 h) getting very low levels, both intracellular and in plasma. This active agent is removed in its conjugated forms glucoronate and sulfonate. Studies have shown a polymorphism in the intestinal absorption and in the hepatic metabolism, depending on the species used in the studies.

Various publications have shown that mono-therapy in the treatment of obesity is not effective, combination therapy being indispensable. Nowadays, the literature mentions different combinations for the treatment of obesity and related health problems, however none of them foresees the use of orlistat-resveratrol or provides data on the advantages of this combination or its dosage, clinical trials aren't mentioned either and on the contrary, they warn of adverse effects that may occur.

For example, international patent application WO 2004/080450 describes the use of orlistat with fibrates however, this combination may cause gastrointestinal and skin problems like puritus, rash or photosensitivity.

Patent application WO 2001/000205 describes the combination of sibutramine and orlistat. This combination can represent a risk to patients because sibutramine has been withdrawn from the market by health authorities due to adverse cardiovascular effects it causes.

Mexican patent application No. MX/a/2007/006092 describes the use of orlistat with simvastatin or atorvastatin to decrease the levels of lipids or fatty acids. Combinations herein may develop rhabdomyolysis.

Mexican patent application No. PA/a/2005/013654 shows the combination of orlistat and bupropion. This combination has the disadvantage that the use of bupropion can cause convulsive episodes and adverse effects on the central nervous system of the patient.

The combination of the present application avoids the problems of the combinations mentioned in the prior art. The use of orlistat together with resveratrol has the following advantages:

Anti-obesity effect.
Induced weight loss.
The use of the combination does not require a low caloric intake.
Induced weight loss in shorter treatment times.
It has tolerable side effects or may even have no side effects.
Induction of a better control of blood pressure.
Stimulation of improved glycemic profile.
Induction of a better control of cholesterol and lipid levels.
The combination provides anti-aging and antioxidant effects.
The combination has cardioprotective effect.
The elimination process of each agent is not affected.
The half life of each agent is not affected.
The doses of orlistat or resveratrol used in the combination may be lower than those used in the usual way.
The combination doesn't cause dependence.
The combination modifies positively the desire of food intake.

SUMMARY OF THE INVENTION

The present invention is directed to a combination and a pharmaceutical composition comprising effective amounts of orlistat, or pharmaceutically acceptable salts thereof, and resveratrol or pharmaceutically acceptable salts thereof.

The present invention also relates to the combination of orlistat, or pharmaceutically acceptable salts thereof, and resveratrol or its pharmaceutically acceptable salts, for the preparation of a medicament for the treatment of diseases of overweight, obesity and related health problems.

Similarly, the invention relates to the process for preparing a pharmaceutical composition comprising orlistat and resveratrol.

BRIEF DESCRIPTION OF THE DRAWINGS

The patent application file contains at least one color drawing. Copies of this patent or patent application publication with color drawings will be provided by the USPTO upon request and payment of the necessary fee.

FIG. 2 corresponds to a graph of weight gain in the experimental groups. Results of the groups: standard diet (NCG), high calorie diet (PCG), high calorie diet administered with orlistat (OHG), high calorie diet administered with resveratrol (RHG), high calorie diet and the administration of the combination of orlistat-resveratrol in two different concentrations (GH combination 1 and GH combination 2).

FIG. 3 is a graph on daily food intake during the study period. Animals treated with standard diet maintain a consistent pattern of food consumption (between 13-15 g) and animals fed with the high calorie diet show a plateau in the consumption of less than 16 g/day.

FIGS. 4A to 4c are graphs of monitored blood pressure during the study period. FIG. 4B shows the course of systolic pressure and FIG. 4C shows the average pressure. These results correspond to all the rats of the experimental groups throughout the 3 weeks. Those animals fed with a high caloric diet showed elevation of the blood pressure levels of up to 25 mmHg, which is assumed as hypertension, a condition which was reversed in week 3 after the treatment with the combination of orlistat-resveratrol.

FIG. 5 is a graph of serum glucose monitoring. It is seen that during the period of 3 weeks, all groups except the one treated with higher doses of the combination of orlistat-resveratrol, showed a considerable increase in serum levels of postprandial glucose.

DESCRIPTION OF THE INVENTION

According to the present invention, there is provided a combination comprising orlistat and resveratrol. The inventors of the present invention have found that the co-administration of these 2 drugs has a synergistic effect in the treatment of diseases like overweight, obesity and related health problems, such as metabolic syndrome, cardiovascular disease, etc.

The inventors of the present invention found that the combination of orlistat with resveratrol has a pharmacological effect in rats with experimental obesity, being a synergistic effect in weight loss. During the study, the results show that the combination of orlistat and resveratrol is effective in weight reduction in comparison to the separate administration of these active agents.

Figure 1:
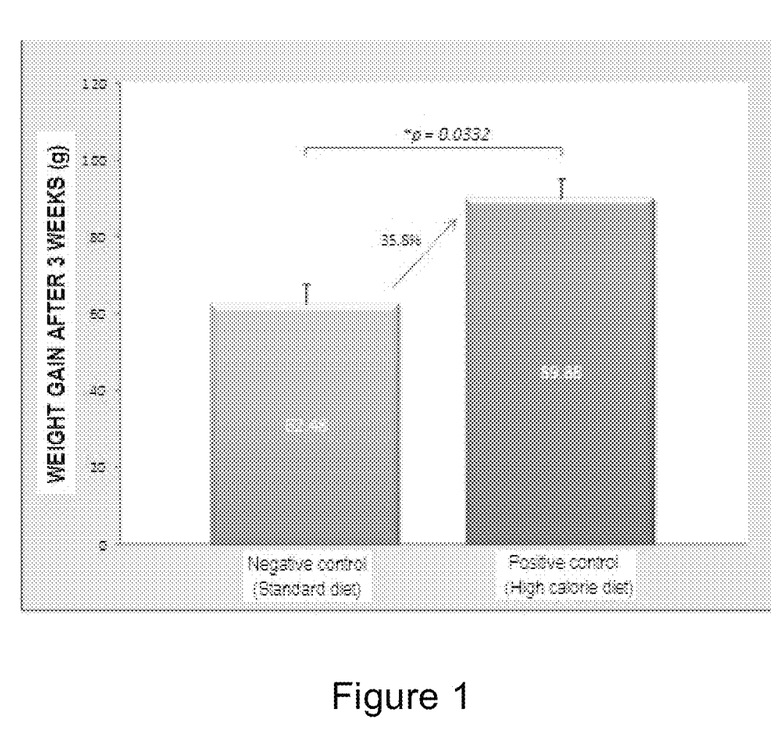
FIG. 1 is a graph showing the status of obesity induced by a high calorie diet in Wistar rats after 3 weeks. The difference in weight between rats with standard diet (negative control group=NCG) and rats with high calorie diet (positive control=PCG) was 35.8.

To demonstrate the aforementioned, a prospective longitudinal preclinical study in female rats was performed randomly. Once the obesity status was reached (difference between positive and negative control higher than 30%) (see FIG. 1), the animals received for 3 weeks oral treatment as follows:

Group 1. Negative control. Standard diet AD libitum and vehicle (saline solution 1 ml/kg) 3 times per day.

Group 2. Positive control. High calorie diet AD libitum and vehicle (saline solution 1 ml/kg) 3 times per day.

Group 3. High calorie diet+orlistat 1.7 mg/kg 3 times per day.

Group 4. High calorie diet+resveratrol 10 mg/kg 3 times per day.

Group 5. High calorie diet+orlistat-resveratrol 1.0 mg/5.0 mg/kg 3 times per day.

Group 6. High calorie diet orlistat-resveratrol 1.7 mg/10.0 mg/kg 3 times per day.

The used doses of orlistat and resveratrol were based on extrapolation of the clinical use of the drug, individually, in humans, meaning that the dose of orlistat (1.7 mg/kg) is equivalent to 120 mg consumed clinically for weight control, and for resveratrol a dose of 10 mg/kg was used. The prior is not limitative to the use of other doses ranging from 30 mg to 360 mg for orlistat and from 100 mg to 2000 mg for resveratrol, preferably 1000 mg.

To receive the treatments, the experimental animals were divided into groups of 2 animals and placed on cages to allow them free access to food and water. Every day at the same time (morning, afternoon and evening), the record of consumption (for both: food and water) was made, and the replacement of initial amount, already established (150 g of food and 250 ml of water), was also carried out. On preset days, the measurement of blood pressure by non-invasive methods was performed too.

The primary endpoint for measuring treatment efficacy was the weight reduction after 3 weeks, although we evaluated the time course of weight gain during this period, as well as the ability of each treatment to reduce excessive weight gain ("obesity").

Rats in all groups were evaluated for spontaneous adverse effects such as reflex reduction, well-walking assessment, corneal reflex before and after drug treatments. Additionally, serum values were determined for oxalacetic and piruvic transminases at the end of the study to evaluate possible hepatic problems.

For the study, Wistar rats received a diet rich in fats and carbohydrates to resemble pathological states of the Zjucker rat, like overweight at an early age (3-5 weeks), hyperlipidemia, hypercholesterolemia, hyperinsulinemia, and development of adipocyte hypertrophy and adipocyte hyperplasia. Wistar rats were given a rich diet in fat and carbohydrates for 3 weeks and the rat is considered to be in an obese state when the difference between the negative and positive control is 30% (see FIG. 1).

Figure 2:
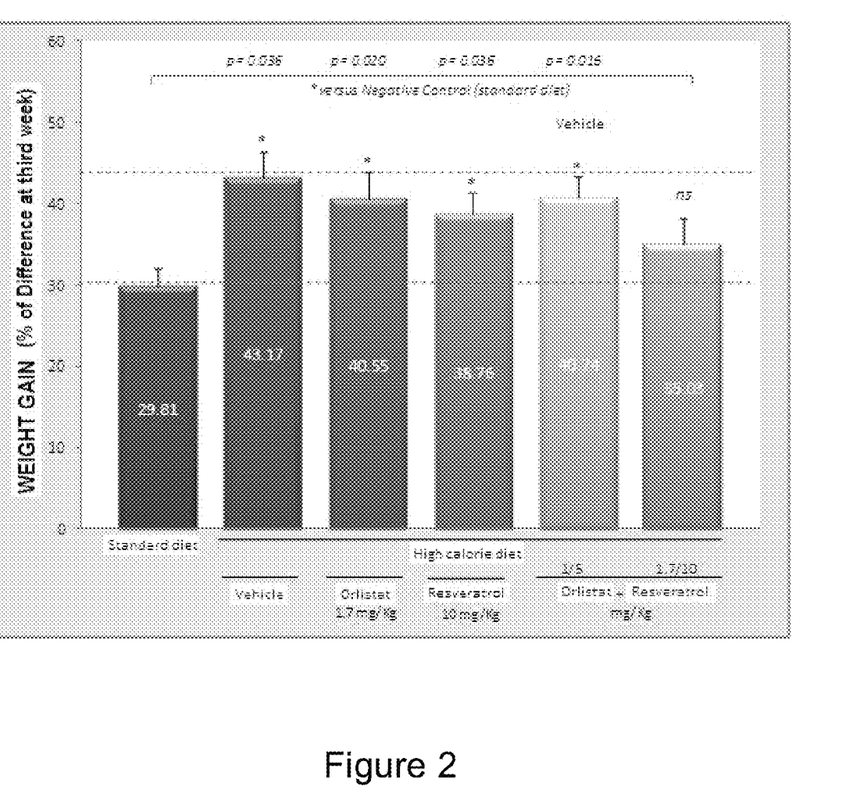

During the study, the results show that the orlistat-resveratrol combination is effective for weight reduction in comparison with separate administration of orlistat and resveratrol (see FIG. 2).

Figure 3:
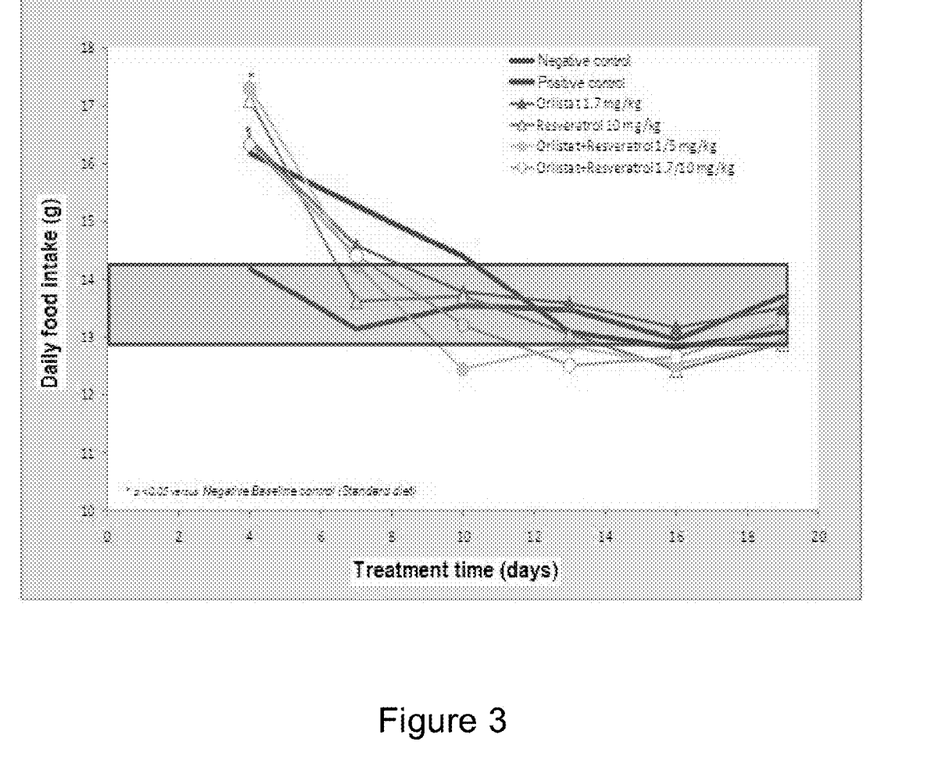

The combination of the present invention as shown in the study, exhibited a positive effect in the reduction of food intake. FIG. 3 shows that while the animals treated with the standard diet maintained a consistent pattern of food intake (13 to 15 mg), animals fed with the high-calorie diet and treated with orlistat-resveratrol showed a plateau in the consumption, that is, they began consuming more than 16 g/day, and as time passed, the intake decreased to 13 to 14 g. This phenomenon could be explained as an attempt to adapt to food from a voracious consumer start due to the palatability of the food.

The follow up was made on the physiological and biochemical cardiovascular indicators (blood pressure, lipid levels and cholesterol) as a way to find the pathophysiological consequences of consumption of a high calorie diet, as well as potential therapeutic effects of the study treatments.

Figure 4A:
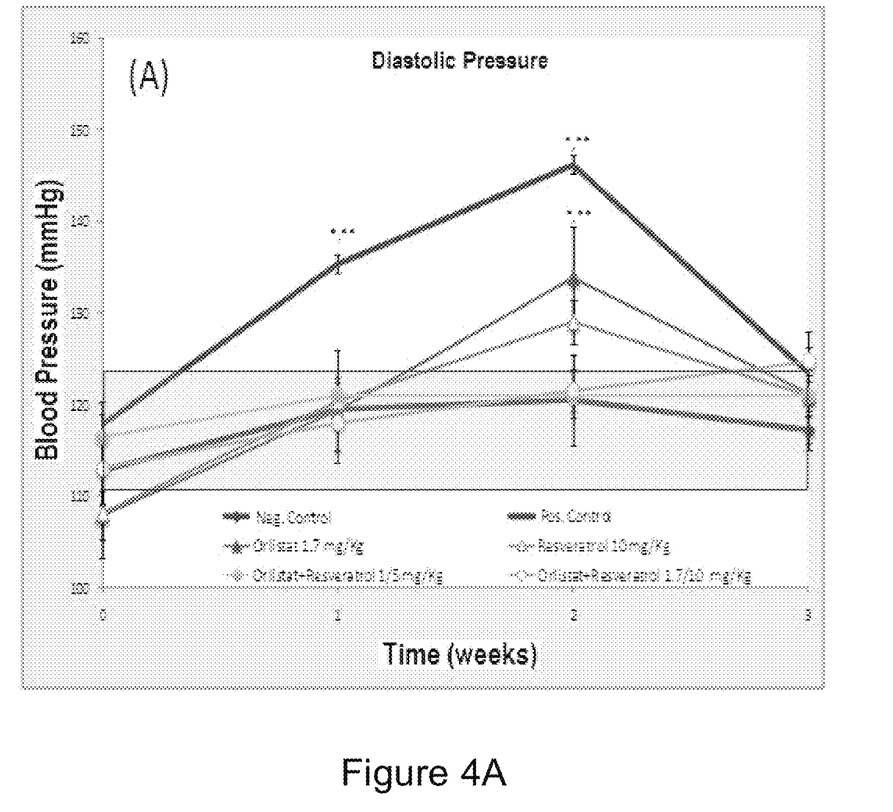
FIG. 4A shows the result of diastolic pressure.
Figure 4B:
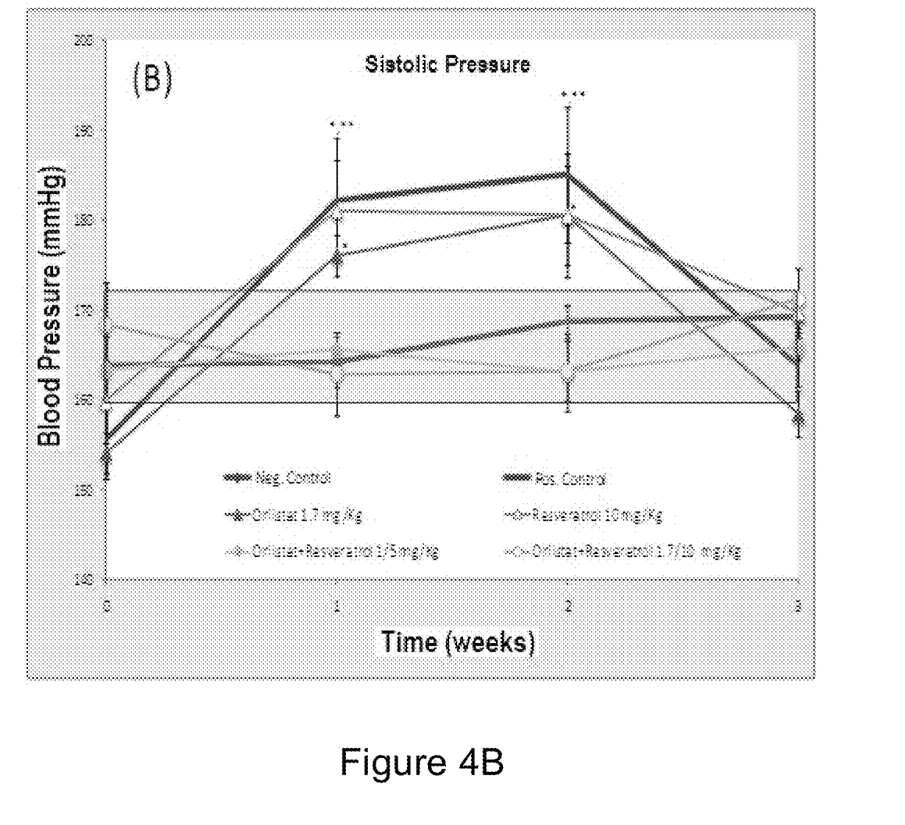
Figure 4C:
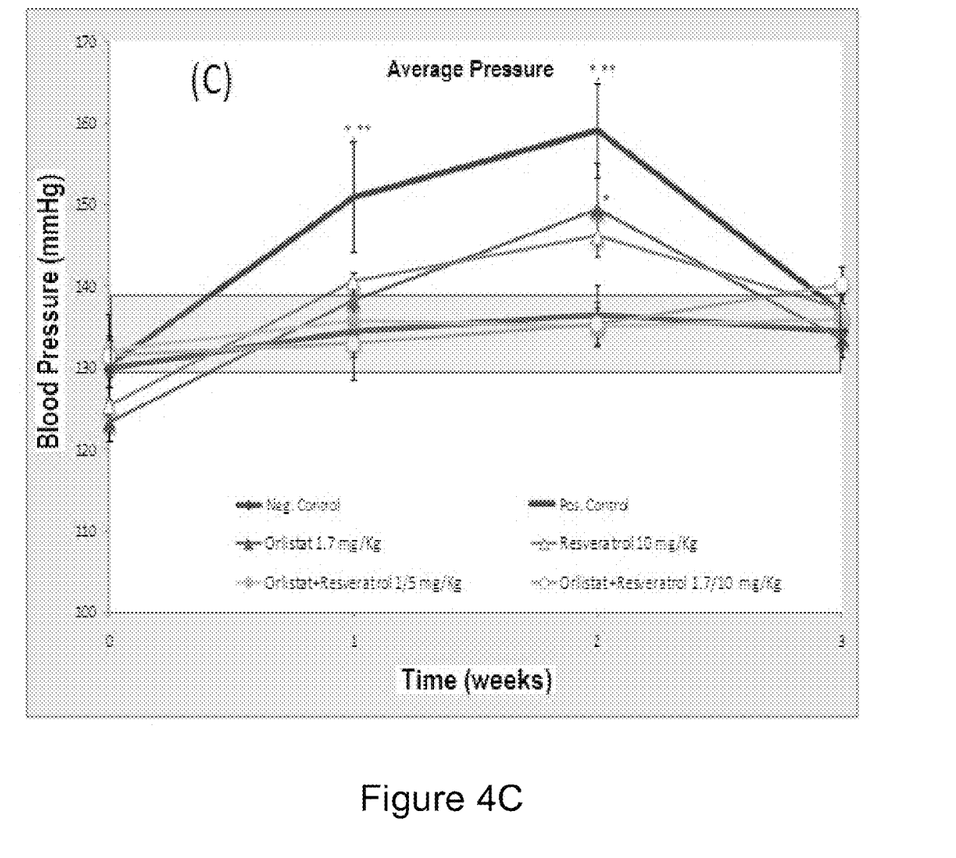

FIGS. 4A to 4C show the time course of systolic, diastolic and mean blood pressure of the rats of all the experimental groups throughout 3 weeks of follow-up. As anticipated, those animals fed with a high calorie diet showed an elevation of the blood pressure levels up to 25 mmHg at week 2, this is, it could be proposed that animals under this condition are under a phase of "hypertension", however this state is reversed after the third week, apparently influenced by weight loss due to the treatment. It is important to observe that the bigger decrease in blood pressure is given by the orlistat-resveratrol combination, however there is an increased effect for the treatment orlistat-resveratrol 1.7/10 mg/kg body weight in the pressure decrease.

Figure 5:
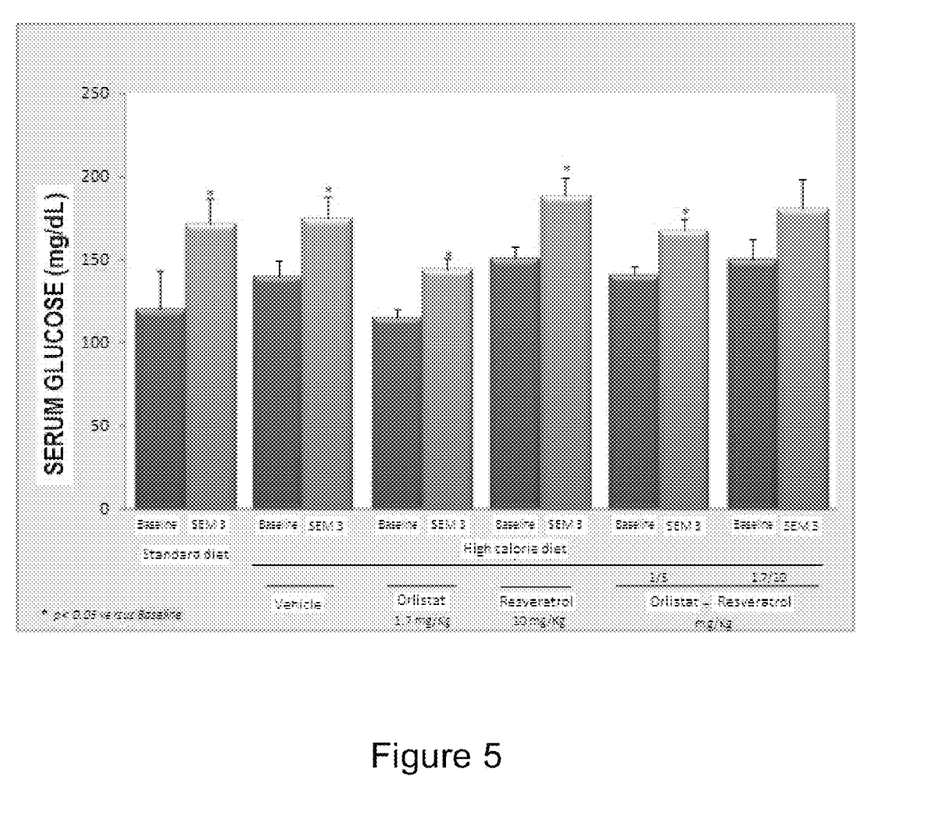

Regarding serum glucose levels, during the evaluation period it is observed that the administered treatments increased postprandial glucose levels, although to a lesser extent than the orlistat-resveratrol combination; apparently the administration of the treatments causes a more efficient management of the available energy, due to the high calorie diet (see FIG. 5).

Figure 6:
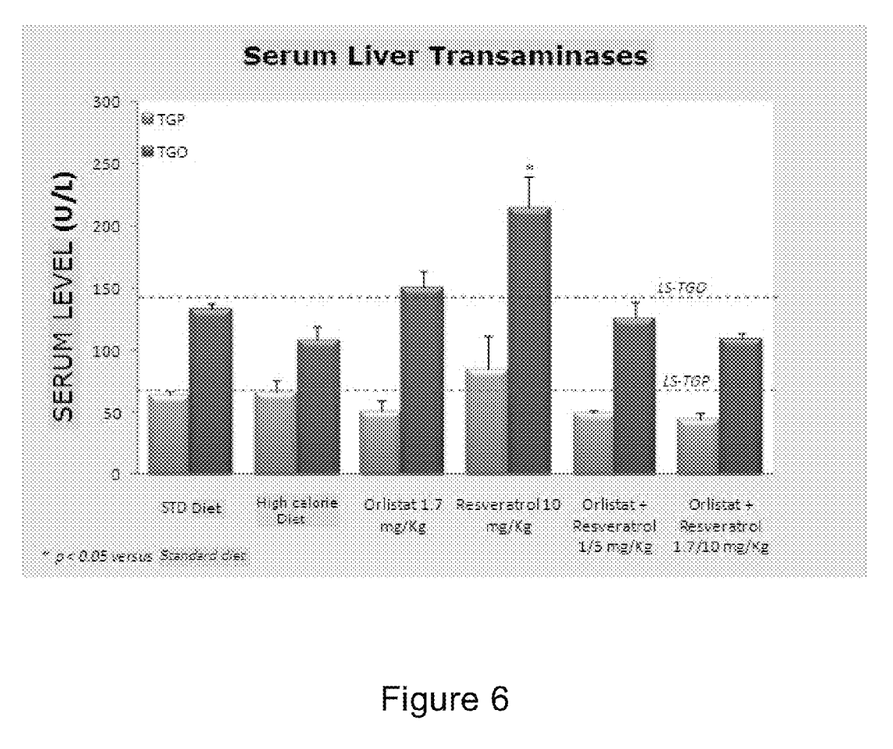
FIG. 6 is a tracking graph of serum liver transaminase. The result shows that the high caloric diet did not alter the activity of any transaminases.

Similarly, the increase of liver transaminases was monitored as indicators of any potential hepatic adverse effect of the treatments. FIG. 6 shows an increase of the transaminase levels using the treatments, compared with the high calorie diet. For the orlistat-resveratrol combination the increase was lower and no animal damages were observed, therefore an enhanced safety of the use of the combination orlistat-resveratol is observed.

The combination of orlistat-resveratrol, or pharmaceutically acceptable salts thereof, is administered in different formulations, a preferred one being the orally-administered formulation for its comfort. It can be presented as a suspension, capsule, tablet, granule, powder, etc.

Now, it is not obvious to combine 2 active ingredients when, due to their physicochemical properties, it is complicated to manufacture a physicochemically stable formulation that meets the required characteristics for administration. In the case of orlistat, its waxy consistency complicates its formulation process when combined with another active ingredient. This is the main reason why it is not possible to find publications that refer to the combination of orlistat-resveratrol.

The present invention provides a stable pharmaceutical composition which, surprisingly, solves formulation problems due to physical and chemical characteristics of orlistat and resveratrol. It should not be forgotten than orlistat melts at approximately 43° C. (40°-44° C.), said temperature is reached during the manufacturing processes, thus complicating significantly the obtention of a stable formulation that meets the requirements for human use and having an acceptable appearance.

The inability to maintain in one single dosage unit both active ingredients was observed due to their different physicochemical properties of orlistat (waxy) and resveratrol (powder), however, the present invention employs a heat-resistant system which allows the coexistence of the active ingredients.

As already mentioned, the low melting point of orlistat complicated considerably the manufacture of an oral dosage form, because during the manufacturing process temperatures above 40° C. were reached, provoking the fusion of the active ingredient orlistat.

The process of the present invention comprises: forming a mixture of orlistat with pharmaceutically acceptable excipients which can be, as non-limitative examples, cellulose derivatives, microcrystalline cellulose, lactose or corn starch; heating the mixture at a temperature of 50 to 70° C.; extruding the mixture and forming spheres or beads comprising orlistat; cooling down the powders; and finally coating the powder blend with a dispersion of resveratrol and a polymer selected from hydroxypropyl methylcellulose, polyvinylpyrrolidone, hydroxypropyl cellulose or cellulose derivatives. This last step of coating the powders can be performed in a fluidized bed equipment or similar.

The combination of the invention can be used for preparing a drug product for the treatment of diseases like overweight, obesity and related health problems. The amount of orlistat used can be between 30 mg to 360 mg, preferably 120 mg. The amount of resveratrol used can vary from 100 mg to 2000 mg, preferably 1000 mg. Orlistat and resveratrol can be together in the same dosage form or may present in different pharmaceutical dosage forms or different dosage units.

The invention has been sufficiently described so that a person of ordinary skill in the art could reproduce and obtain the results mentioned in this document. However, any person skilled in the art to which this invention belongs may be able to make modifications not described in this application. Therefore, if the application of these modifications in a given composition requires the matter claimed in the following clauses, such compositions must fall within the scope of the present invention.

The invention claimed is:

1. A pharmaceutical combination, comprising orlistat, or pharmaceutically acceptable salts thereof, and resveratrol, or pharmaceutically acceptable salts thereof, for controlling weight gain without increasing hepatic transaminase levels, wherein the combination contains a weight relation orlistat/resveratrol of 1.7/10.

2. A pharmaceutical composition, comprising the combination of claim 1 and pharmaceutically acceptable excipients.

3. The pharmaceutical composition according to claim 2, wherein the composition is formulated as an oral composition.

4. A method for controlling weight gain without increasing hepatic transaminase levels, comprising:
administering an effective amount of the combination according to claim 1 to a person in need thereof.

5. The method as claimed in claim 4, wherein the orlistat and resveratrol are present in the same pharmaceutical dosage form.

6. The method as claimed in 4, wherein the orlistat and resveratrol are present in different dosage forms or different dosage units.

* * * * *